US006369083B1

(12) United States Patent
Canada et al.

(10) Patent No.: US 6,369,083 B1
(45) Date of Patent: Apr. 9, 2002

(54) 2-METHOXYIMINO-2 (PYRINYLOXYMETHYL) PHENYL ACETAMIDES WITH POLYETHER DERIVATIVES ON THE PYRIDINE RING

(75) Inventors: Emily J. Canada; Carl P. Denny, both of Indianapolis; Christopher S. Galka; Neil V. Kirby, both of Carmel, all of IN (US); Marc McKennon, Issaquah, WA (US); Mary E. Pieczko; Rebecca L. Rezac, both of Indianapolis, IN (US); Brent J. Rieder, Greenfield, IN (US); John K. Swayze; Chrislyn M. Carson, both of Carmel, IN (US); David D. Johnson, Greenfield, IN (US); Gregory M. Kemmitt, Lafayette, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/397,565

(22) Filed: Sep. 16, 1999

Related U.S. Application Data

(60) Provisional application No. 60/100,493, filed on Sep. 16, 1998.

(51) Int. Cl.[7] ...................... A61K 31/44; C07D 213/69; C07D 417/12; C07D 409/12; C07D 405/12
(52) U.S. Cl. ........................ 514/336; 514/348; 514/336; 514/338; 514/340; 514/342; 546/291; 546/296; 546/297; 546/300; 546/268.7; 546/270.1; 546/280.4; 546/283.4; 546/283.7
(58) Field of Search ................ 514/346, 348, 514/336, 338, 340, 342; 546/291, 296, 297, 300, 268.7, 270, 280.4, 283.4, 283.7

(56) References Cited

U.S. PATENT DOCUMENTS

| 5,021,581 | A | | 6/1991 | Clough et al. ............ 546/309 |
|---|---|---|---|---|
| 5,089,510 | A | | 2/1992 | Tapolczay et al. ........... 514/345 |
| 5,157,037 | A | | 10/1992 | Schuetz et al. ............. 514/269 |
| 5,185,342 | A | | 2/1993 | Hayase et al. .............. 514/274 |
| 5,334,577 | A | | 8/1994 | Wenderoth et al. .......... 504/130 |
| 5,442,063 | A | | 8/1995 | Takase et al. ............... 544/333 |
| 5,466,693 | A | | 11/1995 | Warrington et al. ........ 514/269 |
| 5,585,513 | A | | 12/1996 | Matthews et al. ............ 560/60 |
| 5,770,614 | A | * | 6/1998 | Murabayishi et al. ....... 514/348 |
| 5,856,573 | A | | 1/1999 | Takase et al. ............... 564/169 |

FOREIGN PATENT DOCUMENTS

| EP | 0 781 764 A1 | 7/1997 |
|---|---|---|
| WO | WO 97/01538 | 1/1997 |
| WO | WO 97/29088 | 8/1997 |
| WO | W0 98/23350 | 6/1998 |
| WO | WO 98/33772 | 8/1998 |
| WO | WO 99/25713 | 5/1999 |

OTHER PUBLICATIONS

"Strobilurins: Evolution of a New Class of Active Substances", Angew Chem. Int. Ed. 1999, 38. 1328–1349.

"The Strobilurin Fungicides", Fugicidal Activity, 1998.

"Structure and Fungicidal Activities of 2–Methoxyimino–N– methyl–2–[2–(substituted pyridyloxymethyl)phenyl] acetamide Derivatives", J. Petsticide Sci. 23. 379–385 (1998).

Extended Summaries: IUPAC Congress, Pestic Sci 55: 343–389 (1999).

* cited by examiner

Primary Examiner—Alan L. Rotman
(74) Attorney, Agent, or Firm—Carl D. Corvin

(57) ABSTRACT

The present invention provides novel 2-methoxyimino-2-(pyridinyloxymethyl) phenyl acetamide compounds with polyether substituents on the pyridine ring, their use as fungicidal compounds, and their use in fungicidal compositions comprising at least one of the 2-methoxyimino-2-(pyridinyloxymethyl)phenyl acetamide compounds as the active ingredient.

12 Claims, No Drawings

2-METHOXYIMINO-2 (PYRINYLOXYMETHYL) PHENYL ACETAMIDES WITH POLYETHER DERIVATIVES ON THE PYRIDINE RING

PRIORITY CLAIM

This application claims a priority based on provisional application No. 60/100,493 which was filed in the U.S. Patent and Trademark Office on Sep. 16, 1998.

BACKGROUND OF THE INVENTION

The present invention provides novel 2-methoxyimino-2-(pyridinyloxymethyl)phenyl acetamide compounds with polyether substituents on the pyridine ring, their use as fungicidal compounds, and their use in fungicidal compositions comprising at least one of the 2-methoxyimino-2-(pyridinyloxymethyl)phenyl acetamide compounds as the active ingredient.

SUMMARY OF THE INVENTION

This invention provides novel 2-methoxyimino-2-(pyridinyloxymethyl)phenyl acetamide compounds of formula (1), below

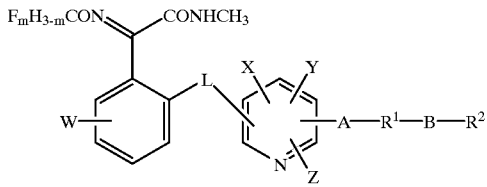

Formula (1)

wherein m is an integer 0–3;

L is —O—, —CH$_2$—, —SO$_n$—, -CH$_2$O—, —OCH$_2$—, —CH$_2$S—, —SCH$_2$—, —CH=CH—, —C≡C—, or

wherein n is an integer 0–2;

X, Y, and Z are each independently H, C$_{1-6}$ alkyl, C$_{1-6}$ alkoxy, halo-C$_{1-6}$ alkyl, halo-C$_{1-6}$ alkoxy, halo, nitro, carbo-C$_{1-6}$ alkoxy, cyano, C$_{1-6}$ alkylthio, or halo-C$_{1-6}$ alkylthio;

W is H, halogen, C$_{1-4}$ alkyl, C$_{1-4}$ alkoxy, halo-C$_{1-4}$ alkyl, or C$_{1-4}$ alkylthio;

A is O, S, NR$^3$, OCH$_2$, SCH$_2$;

B is O or S;

R$^1$ is a C$_1$–C$_4$ alkyl group (optionally substituted by alkenyl, cycloalkyl, alkoxy, alkoxycarbonyl, arylalkyl, cyano, cyanoalkyl, halo, or haloalkyl), optionally substituted phenyl, or an optionally substituted aryl or heteroaryl ring;

R$^2$ is a C$_1$–C$_8$ alkyl, (optionally substituted by alkenyl, cycloalkyl, alkoxy, alkoxycarbonyl, arylalkyl, cyano, cyanoalkyl, halo, or haloalkyl), optionally substituted phenyl, or an optionally substituted aryl or heteroaryl ring;

or the group R$^1$—B—R$^2$ can be an optionally substituted 4–6 membered saturated or unsaturated heterocyclic ring;

or the group —A—R$^1$—B—R$^2$ can be an optionally substituted 4–6 membered saturated or unsaturated heterocyclic ring containing 2 or more heteroatoms; and R$^3$ is H or C$_{1-6}$ alkyl.

The present invention also provides compositions comprising one or more compounds of Formula (1) in combination with phytologically-acceptable carriers and/or diluents. Methods for the use of compounds of formula (1) and compositions comprising one or more compounds of formula (1) are also provided.

DETAILED DESCRIPTION OF THE INVENTION

Throughout this document, all temperatures are given in degrees Celsius and all percentages are weight percentages, unless otherwise stated.

The term "halogen" or "halo" refers to F, Cl, I, or Br.

The term "alkyl", "alkenyl", or "alkynyl" refers to a straight chain or branched chain carbon radical containing the designated number of carbon atoms.

The term "alkoxy" refers to a straight or branched chain alkoxy group.

The term "halo alkyl" refers to a straight or branched alkyl group substituted with one or more halo atoms. The term "halo alkoxy" refers to an alkoxy group substituted with one or more halo atoms.

The term "aryl" or "Ph" refers to a phenyl group. The term "substituted aryl" refers to a phenyl group substituted with C$_1$–C$_6$ alkyl, C$_1$–C$_6$ alkoxy, halo-C$_1$–C$_6$ alkyl, halo-C$_1$–C$_6$ alkoxy, halo, nitro, carbo-C$_1$–C$_6$ alkoxy, or cyano. The term "heteroaryl" refers to pyridyl, pyridinyl, pyrazinyl, pyridazinyl or thiophene.

The term "Me" refers to a methyl group. The term "Et" refers to an ethyl group. The term "Pr" refers to a propyl group. The term "Bu" refers to a butyl group. The term "EtOAc" refers to ethyl acetate.

The term "ppm" refers to parts per million. The term "psi" refers to pounds per square inch.

The term "M.P." refers to melting point. The term "bp" refers to boiling point.

While all the compounds of this invention have fungicidal activity, certain classes of compounds may be preferred for reasons such as, for example, greater efficacy or ease of synthesis.

A preferred class includes those compounds of Formula (2), below

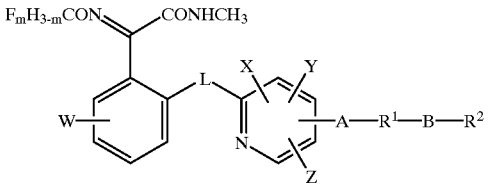

Formula (2)

wherein the substituents are as defined in Formula (1), above.

A more preferred class includes those compounds of Formula (3), below

Formula (3)

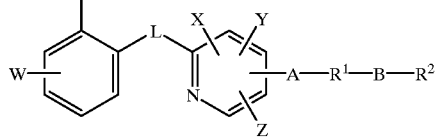

wherein L is either —O—, —CH$_2$O—, or —OCH$_2$—, and the other substituents are as defined in Formula (1), above.

A next more preferred class includes those compounds of Formula (4), below

Formula (4)

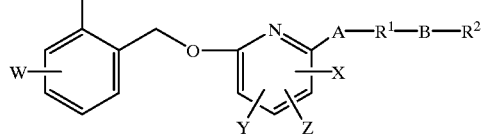

wherein the substituents are as defined in Formula (1), above.

A next more preferred class includes those compounds of Formula (5), below

Formula (5)

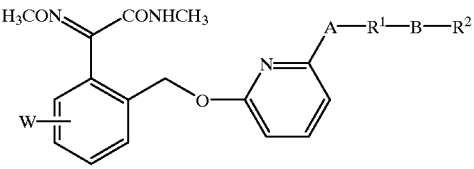

wherein the substituents are as defined in Formula (1), above.

A next more preferred class includes those compounds of Formula (5-1), below

Formula (5-1)

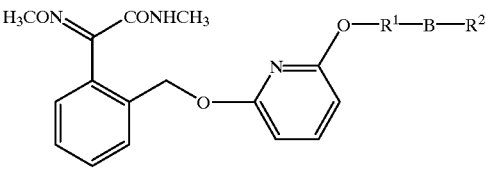

wherein the substituents are as defined in Formula (1), above.

EXAMPLES

Compounds of the present invention may be prepared by routes commonly known in the art using commercially available or readily synthesized starting materials. Such general procedures are described in Scheme 1 and Scheme 2, below, wherein the substituents are as described in formula (1), above, and V is a leaving group, such as, for example, F, Cl, or SO$_2$CH$_3$.

Scheme 1

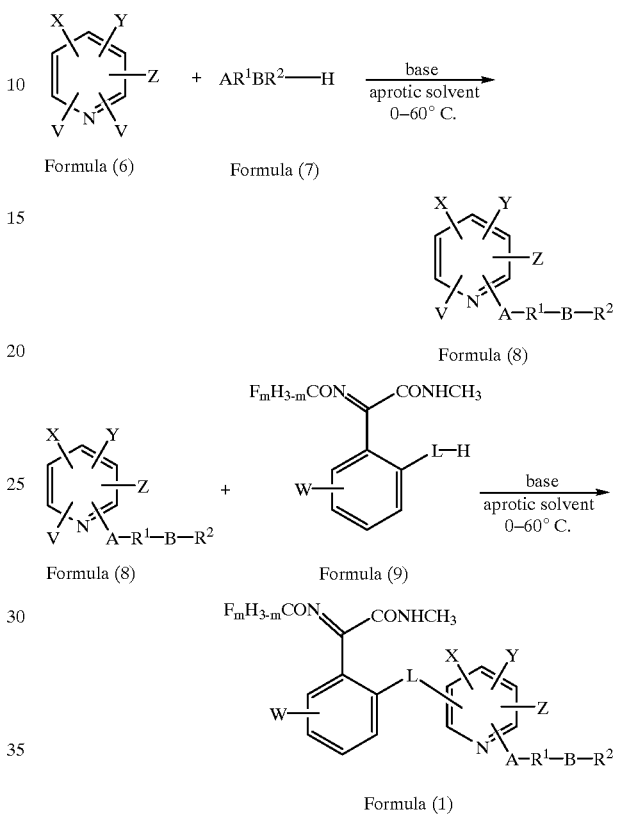

An compound of formula (7) is reacted with an appropriately substituted pyridine derivative of formula (6) in the presence of a base in an aprotic solvent. Examples of an appropriate solvent for this reaction would include, but are not restricted to, tetrahydrofuran, dimethyl sulphoxide, acetone, acetonitrile, dimethyl formamide, N-methylpyrrolidinone. Examples of an appropriate base for this reaction would include, but are not restricted to, sodium hydride, potassium hydride, potassium t-butoxide, potassium carbonate, or a tertiary amine derivative such as triethylamine.

The intermediate so formed is then reacted with a compound of formula (9) in the presence of a base in an aprotic solvent. Examples of an appropriate solvent for this reaction would include, but are not restricted to, tetrahydrofuran, dimethyl sulphoxide, acetone, acetonitrile, dimethyl formamide, N-methylpyrrolidinone. Examples of an appropriate base for this reaction would include, but are not restricted to, sodium hydride, potassium hydride, potassium carbonate, potassium t-butoxide, or a tertiary amine derivative such as triethylamine.

Scheme 2

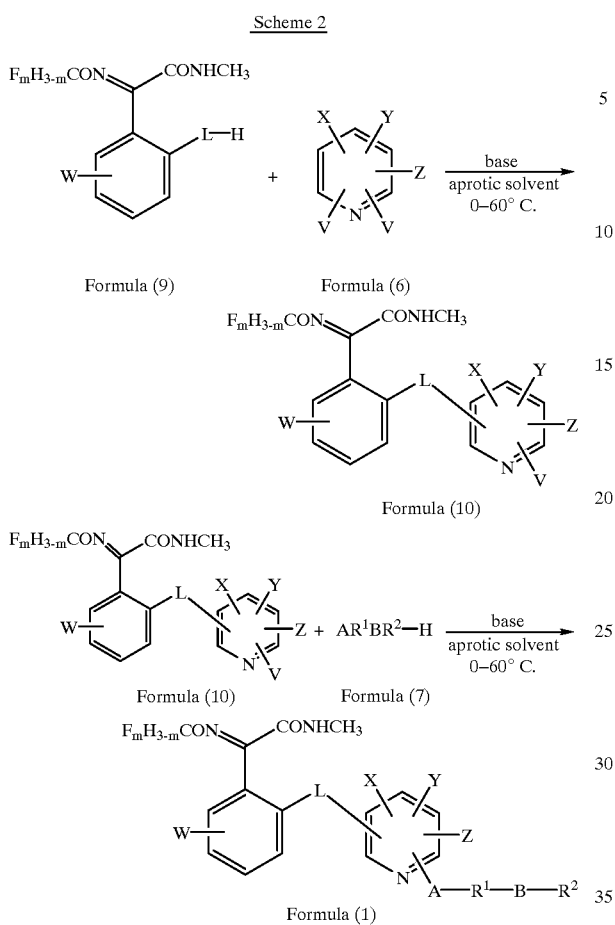

A compound of formula (9) is reacted with an appropriately substituted pyridine derivative of formula (6) in the presence of a base in an aprotic solvent. Examples of an appropriate solvent for this reaction would include, but are not restricted to, tetrahydrofuran, dimethyl sulphoxide, acetone, acetonitrile, dimethyl formamide, N-methylpyrrolidinone. Examples of an appropriate base for this reaction would include, but are not restricted to, sodium hydride, potassium hydride, potassium carbonate, potassium t-butoxide, or a tertiary amine derivative such as triethylamine.

The intermediate so formed is then reacted with a compound of formula (7) in the presence of a base in an aprotic solvent. Examples of an appropriate solvent for this reaction would include, but are not restricted to, tetrahydrofuran, dimethyl sulphoxide, acetone, acetonitrile, dimethyl formamide, N-methylpyrrolidinone. Examples of an appropriate base for this reaction would include, but are not restricted to, sodium hydride, potassium hydride, potassium carbonate, potassium t-butoxide, or a tertiary amine derivative such as triethylamine.

The following examples further illustrate this invention. The examples should not be construed as limiting the invention in any manner.

Example 1

2-Fluoro-6-(2.2-dimethyl-1,3-dioxolane-4-methoxy)pyridine

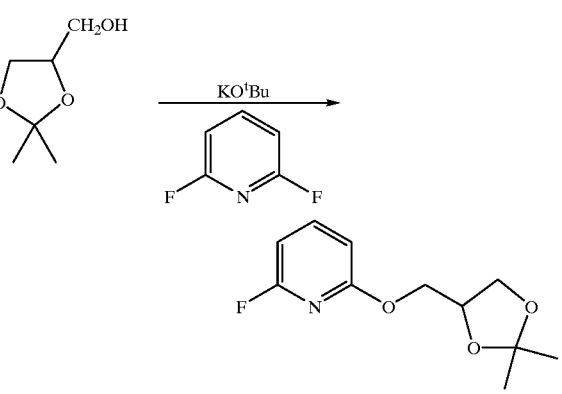

Potassium tert-butoxide (2.14 g, 19.1 mmol) was added to a solution of 2,2-dimethyl-1,3-dioxolane-4-methanol (2.40 g, 18.2 mmol) in 50 mL THF. The resulting mixture was added slowly to a solution of 2,6-difluoropyridine (2.08 g, 18.2 mmol) in THF (50 mL) which was stirred while cooling in an ice bath. After returning the mixture slowly to room temperature and stirring overnight, the mixture was quenched with brine and extracted with EtOAc. Combined extracts were dried with $Na_2SO_4$, then concentrated to dryness. Silica gel column chromatography (10–20% EtOAc in hexane) yielded 2-fluoro-6-((2,2-dimethyl-1,3-dioxolanyl)-4-methoxy)pyridine (2.75 g, 67%)as a clear oil.

Example 2

Benzeneacetamide, 2-[[[6-((2,2-dimethyl-1,3-dioxolanyl)-4-methoxy)-2-pyridinyl]oxy]methy]-α-(methoxyimino)-N-methyl-

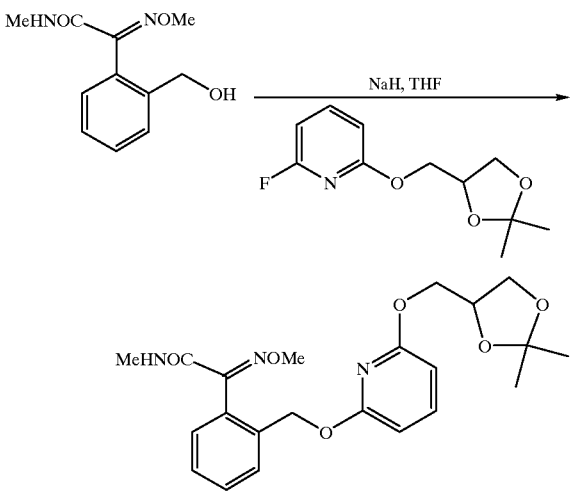

2-(Hydroxymethyl)-α-(methoxyimino)-N-methyl-benzeneacetamide (1.00 g, 4.50 mmol) was dissolved in 10 mL THF, then treated slowly with NaH (0.36 g, 60% oil dispersion, 9.0 mmol) while cooling in an ice bath. Then, 2-fluoro-6-((2,2-dimethyl-1,3-dioxolanyl)-4-methoxy)pyridine (1.23 g, 5.40 mmol) in 10 mL THF was added dropwise, and the bath was allowed to return to room temperature overnight. The mixture was stripped to dryness in vacua, resuspended in 20 mL DMSO, and stirred at room temperature overnight, then it was heated to 50° C. for one hour, followed by stirring at room temperature overnight. Another portion of NaH (0.36 g, 60% oil dispersion, 9.0 mmol) was added, and the mixture was stirred at room temperature overnight. After workup as above with brine and EtOAc, the concentrated extract was purified by silica gel column chromatography (10–50% EtOAc in hexane) to yield the product (0.76 g, 39%) as an oil.

Example 3

Benzeneacetamide, 2-[[[6-fluoro-2-pyridinyl]oxy]methyl]-α-(methoxyimino)-N-methyl-

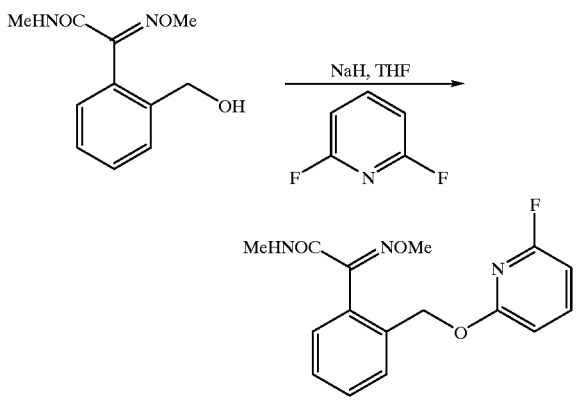

NaH (7.0 g, 60% oil dispersion, 0.176 mol) was added portionwise over five minutes to a stirred slurry of 2-(hydroxymethyl)-α-(methoxyimino)-N-methyl-benzeneacetamide (35.8 g, 0.161 mol) in 700 mL THF. After the resulting mixture was stirred for 3.25 hours, 2,6-difluoropyridine (15.4 g, 0.134 mol) was added neat over a 20 minute period, and the mixture was stirred overnight at room temperature. Water (250 mL) was added, THF was removed in vacuo, and the aqueous residue was extracted three times with 250 mL CH₂Cl₂. The combined extracts were washed with brine (250 mL), filtered through Na₂SO₄, and concentrated in vacuo. The residue was purified by silica gel chromatography (5% CH₃CN in CH₂Cl₂) to yield 2-[[[6-fluoro-2-pyridinyl]oxy]methyl]-α-(methoxyimino)-N-methyl-benzeneacetamide (33.2 g, 78%).

Example 4

Benzeneacetamide, 2-[[[6-((2,2-dimethyl-1,3-dioxolanyl)-4-methoxy)-2-pyridinyl]oxy]methyl-α-(methoxyimino)-N-methyl-

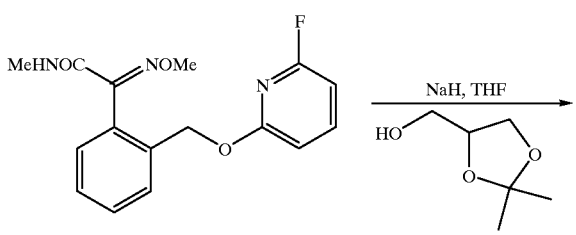

-continued

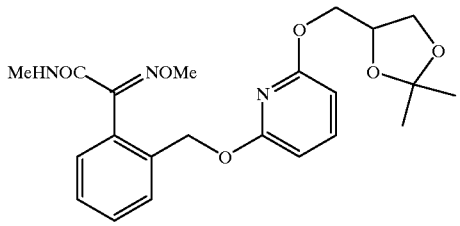

Two portions of NaH (total 4.1 g, 60% oil dispersion, 0.102 mol) were added to a stirred solution of 2,2-dimethyl-1,3-dioxolane-4-methanol (13.3 g, 0.102 mol) in 400 mL THF. The mixture was stirred two hours at room temperature, becoming gelatinous. 2-[[[6-Fluoro-2-pyridinyl]oxy]methyl]-α-(methoxyimino)-N-methyl-benzeneacetamide (27.0 g, 0.0851 mol) was added neat in one portion, then the resulting cloudy gold solution was stirred at room temperature one hour, heated to 55° C. for 3 hours, and stirred at room temperature overnight. Water (250 mL) was added, the layers were separated, and THF was removed from the organic layer in vacuo. The residue was taken up in CH₂Cl₂, then partitioned against the original aqueous phase. The aqueous phase was then extracted four times with 125 mL CH₂Cl₂. All CH₂Cl₂ fractions were combined, washed with brine (250 mL), filtered through Na₂SO₄, and concentrated in vacuo to crude product. The crude product was purified through silica gel chromatography (3–8% CH₃CN in CH₂Cl₂) to yield the product (22.7 g, 60%) as an oil.

Example 5

2-Fluoro-6-(2-propoxyethoxy)pyridine

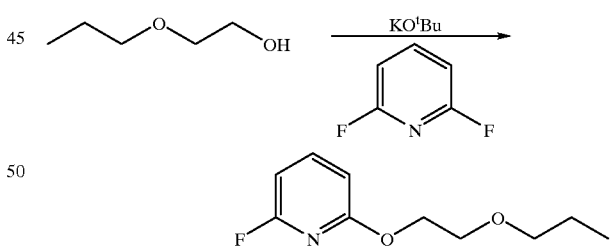

2-Propoxyethanol (1.89 g, 18.1 mmol) was dissolved in 50 mL THF, treated with potassium tert-butoxide (3.05 g, 27.2 mmol), stirred to uniform solution, placed in an addition funnel, and added dropwise to a solution of 2,6-difluoropyridine in 50 mL THF. After stirring overnight at room temperature, the solution was diluted with brine and extracted with ether. The ether extracts were combined and dried over Na₂SO₄, then concentrated in vacuo to yield 2-fluoro-6-(2-propoxyethoxy)-pyridine (3.33 g, 93%) as a yellow oil.

Example 6

Benzeneacetamide, 2-[[[6-(2-propoxyethoxy)-2-pyridinyl]oxy]methyl]-α-(methoxyimino)-N-methyl-

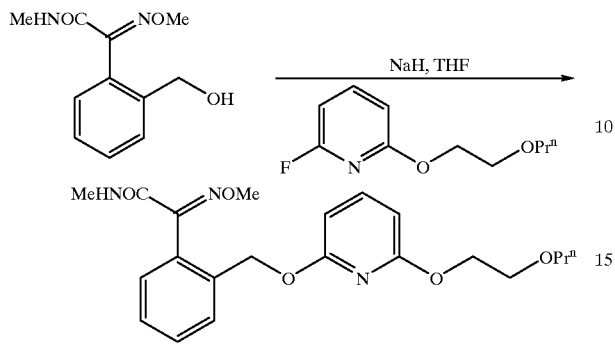

2-(Hydroxymethyl)-α-(methoxyimino)-N-methyl-benzeneacetamide (1.11 g, 5.00 mmol) was dissolved in 100 mL DMSO, then treated portionwise with NaH (0.40 g, 60% oil dispersion, 10 mmol) while stirring to a cloudy solution. 2-Fluoro-6-(2-propoxyethoxy)pyridine (1.20 g, 6.00 mmol) was added, and the mixture was stirred overnight at room temperature. The mixture was diluted with brine and extracted with EtOAc. The combined EtOAc extracts were dried over $Na_2SO_4$ and concentrated in vacuo and the residue was purified by silica gel chromatography (0–50% EtOAc in hexane) to yield the product (0.90 g, 43%) as an oil.

Example 7

Benzeneacetamide, 2-[[[6-(2-propoxyethoxy)-2-Pyridinyl]oxy]methyl]-α-(methoxyimino)-N-methyl-

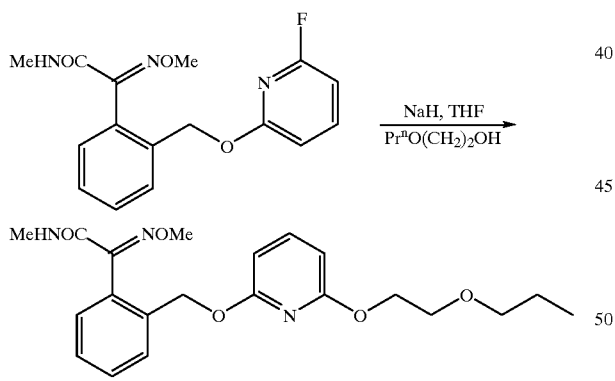

2-Propoxyethanol (12.5 g, 0.12 mol) was dissolved in 500 mL THF, treated with NaH (4.8 g, 60% oil dispersion, 0.12 mol) portionwise over 5 minutes, and stirred at room temperature for two hours. 2-[[[6-Fluoro-2-pyridinyl]oxy]methyl]-α-(methoxyimino)-N-methyl-benzeneacetamide (31.7 g, 0.1 mol) was added portionwise over 10 minutes, then the mixture was stirred at room temperature for one hour, heated to 55° C. for one hour, and stirred to room temperature overnight. The reaction was quenched with 400 mL water, stripped of THF in vacuo, and extracted 3 times with 300 mL $CH_2Cl_2$. The combined extracts were dried over $Na_2SO_4$, filtered, and concentrated in vacuo to yield an oil. This residue was purified via silica gel chromatography (pentane:EtOAc, 2:1) to yield an oil which was dried in vacuo, then triturated with a small amount of ether to yield the product (22.2 g, 55%) as a white powder after drying. M.P. 53–540° C.

Example 8

Benzeneacetamide, 2-[[[6-(2-(2-ethoxyethoxy)ethoxy)-2-pyridinyl]oxy]methyl]-α-(methoxyimino)-N-methyl-

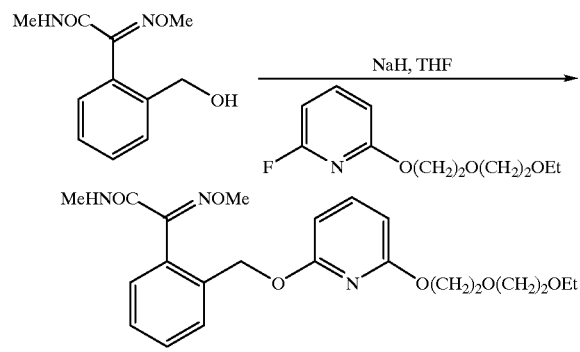

2-(Hydroxymethyl)-α-(methoxyimino)-N-methyl-benzeneacetamide (0.62 g, 2.8 mmol) in 10 mL THF was treated portionwise with NaH (0.22 g, 60% oil dispersion, 5.6 mmol) while cooling in an ice bath. 2-Fluoro-6-(2-(2-ethoxyethoxy)ethoxy)pyridine (1.00 g, 3.35 mmol) was added, and the mixture was allowed to return to room temperature. After 3 hours, the mixture was diluted with brine, treated with sufficient dilute HCl to render it weakly acidic, and extracted with EtOAc. The combined EtOAc extracts were dried over $Na_2SO_4$, then concentrated in vacuo. The residue was purified via silica gel chromatography (0–50w EtOAc in hexane) to yield the product (0.65 g, 54%) as an oil.

Example 9

Benzeneacetamide, 2-[[[6-(2-(2-(1-methylethoxy)ethoxy)-2-Pyridinyl]oxy]methyl]-α-(methoxyimino)-N-methyl-

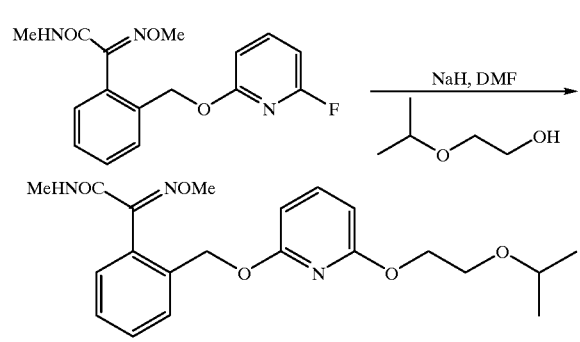

Sodium hydride (0.29 g, 60% oil dispersion, 7.2 mmol) was washed with hexane, then suspended in 20 mL DMF. 2-(1-Methylethoxy)ethanol (0.75 g, 7.2 mmol), dissolved in 5 mL DMF, was added to the NaH suspension over 5 minutes, then the mixture was stirred at room temperature for 40 minutes. This mixture, with the aid of 20 mL additional DMF, was added to a stirred solution of 2-[[[6- fluoro-2-pyridinyl]oxy]methyl]-α-(methoxyimino)-N-methyl-benzeneacetamide (2.28 g, 7.2 mmol) in 30 mL DMF. The reaction was stirred at room temperature one hour, then heated to 60° C. for 19 hours. Additional 2-(1-methylethoxy)ethanol (2.50 g, 24.0 mmol) was dissolved in 30 mL DMF, treated with NaH (0.96 g, 60% oil dispersion), stirred for 5–10 minutes, and transferred to the above reaction mixture. The new mixture was heated to 60° C. for one hour, then diluted with 800 mL water. The aqueous suspension was extracted twice with 100 mL ether, then twice with 60 mL ether. The combined ether extracts were washed twice with 100 mL water, diluted with 150 mL hexane, filtered through phase-separating paper, concentrated in vacuo, and concentrated twice more with 100 mL toluene. The residue was purified over silica gel (step gradient: 4, 5, 8, and 10% $CH_3CN$ in $CH_2Cl_2$) to yield the product (1.04 g, 36%) as an oil.

Example 10

2,3-Dichloro-6-(2-ethoxyethoxy)pyridine & 3,6-Dichloro-2-(2-ethoxyethoxy)pyridine

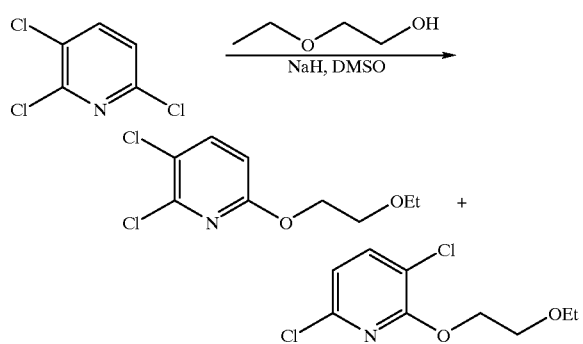

2,3,5-Trichloropyridine (9.12 g, 0.050 mol) and 2-ethoxyethanol (5.40 g, 0.060 mol) were dissolved in 50 mL DMSO, followed by portionwise addition of NaH (2.4 g, 60% dispersion in oil, 0.060 mol). The mixture was heated to 80° C. for 3 hours, stirred at room temperature overnight, then heated to 120° C. for 5 hours. The reaction mixture was then diluted to 900 mL with brine, and extracted three times with 100 mL ether. The ether extracts were combined, washed twice with 100 mL water, diluted with 300 mL hexane, filtered through phase-separating paper, and concentrated in vacuo. The residue was purified via silica gel chromatography (first column with 10–50% EtOAc in hexane; second column with 0–10% EtOAc in hexane). Concentration of pure fractions gave 3,6-dichloro-2-(2-ethoxyethyl)pyridine as the major isomer (5.78 g white solid, M.P. 33–34° C.) and 2,3-dichloro-6-(2-ethoxyethyl)pyridine as the minor isomer (1.43 g white solid, M.P. 47–480° C.).

Example 11

3-Chloro-2-(2-ethoxyethoxy)-6-(methylthio)pyridine

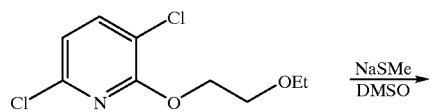

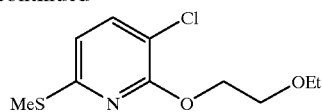

3,6-Dichloro-2-(2-ethoxyethyl)-pyridine (1.18 g, 5.00 mmol) was dissolved in 25 mL DMSO, treated with $NaSCH_3$ (0.53 g, 7.5 mmol), and stirred at room temperature overnight. The mixture was diluted with brine, then extracted with EtOAc. The combined EtOAc extracts were combined, dried over $Na_2SO_4$, and concentrated in vacuo to yield 3-chloro-2-(ethoxyethyl)- 6-(methylthio)pyridine (0.91 g, 76%) as a yellow oil, used without further purification.

Example 12

3-Chloro-2-(2-ethoxyethoxy)-6- -(methylsulphonyl)pyridine

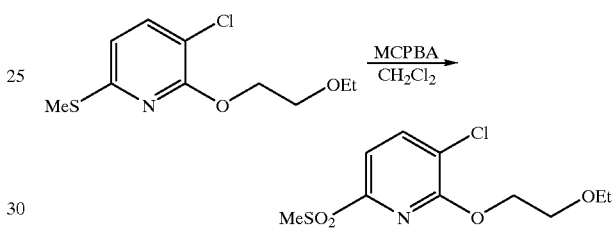

3-Chloro-2-(ethoxyethyl)-6-(methylthio)pyridine (0.91 g, 3.7 mmol) was dissolved in 25 mL $CH_2Cl_2$, cooled in an ice bath, and was treated with m-chloroperoxybenzoic acid (MCPBA; 2.53 g of reagent estimated to be 50–55% pure, ca. 7.3–8.0 mmol) added dropwise in 25 mL $CH_2Cl_2$. The reaction was allowed to return to room temperature and stirred overnight. After dilution with more $CH_2Cl_2$, the mixture was washed with saturated $Na_2CO_3$, then water, and was concentrated to yield 3-chloro-2-(ethoxyethyl)-6-(methylsulphonyl)pyridine (0.60 g, 58%) as a clear oil, used without further purification.

Example 13

Benzeneacetamide, 2-[[[5-chloro-6-(2-ethoxyethoxy)-2-pyridinyl]oxy]methyl]-α-(methoxyimino)-N-methyl-

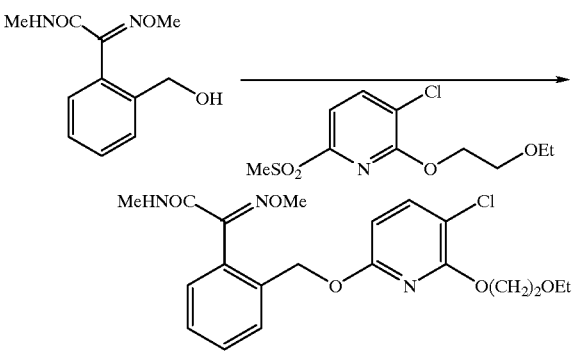

2-(Hydroxymethyl)-(-(methoxyimino)-N-methyl-benzeneacetamide (0.60 g, 2.1 mmol) was dissolved in 20 mL DMSO, treated portionwise with NaH (0.14 g, 60% oil dispersion, 3.6 mmol), and stirred. 3-Chloro-2-(ethoxyethyl)-6-(methylsulphonyl)pyridine was dissolved in 25 mL DMSO, then added dropwise to the above mixture. After stirring at room temperature overnight, the reaction was quenched with brine and extracted with EtOAc. The EtOAc extracts were combined, dried over $Na_2SO_4$, and concentrated in vacuo. The residue was purified via silica gel chromatography (25–60% EtOAc in hexane) to yield the product (0.27 g, 30%), M.P. 94–96° C.

The following tables identify various compounds of the illustrated general formulas prepared analogous to the procedures illustrated in the preceding examples:

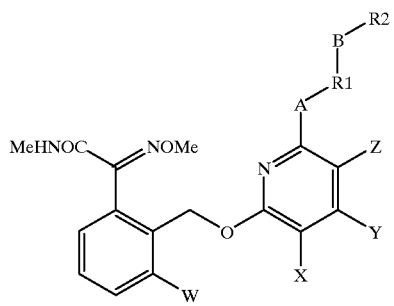

| Compound number | W | X | Y | Z | A | $R^1$—B—$R^2$ |
|---|---|---|---|---|---|---|
| 1 | H | Cl | H | Cl | $OCH_2$ | 2,2-dimethyl-1,3-dioxolan-4-yl |
| 2 | H | H | H | H | $OCH_2$ | 2,2-dimethyl-1,3-dioxolan-4-yl |
| 3 | H | Cl | H | Cl | $OCH_2$ | 2-furyl (E-isomer) |
| 4 | H | Cl | H | Cl | $OCH_2$ | 2-furyl (Z-isomer) |

| Compound number | W | X | Y | Z | A | $R^1$—B—$R^2$ |
|---|---|---|---|---|---|---|
| 5 | H | H | H | H | $OCH_2$ | 2-furyl |
| 6 | H | H | H | H | $OCH_2$ | 2-methyl-2-trifluoromethyl-1,3-dioxolan-4-yl |
| 7 | H | H | H | H | $OCH_2$ | 3-methyloxetan-3-yl |
| 8 | H | H | H | H | $OCH_2$ | 2-furyl |
| 9 | H | H | H | H | $OCH_2$ | 2-tetrahydropyranyl |
| 10 | H | H | H | H | $OCH_2$ | 2-tetrahydrofuranyl |
| 11 | H | H | H | H | $OCH_2$ | 2,2-di(trifluoromethyl)-1,3-dioxolan-4-yl |
| 12 | H | H | H | H | S | 5-methylthio-1,3,4-thiadiazol-2-yl |
| 13 | H | H | H | H | S | 7-ethoxybenzo-thiazol-2-yl |
| 14 | H | H | H | H | O | 2-tetrahydropyranyl |
| 15 | H | H | H | H | S | 2-thienyl |

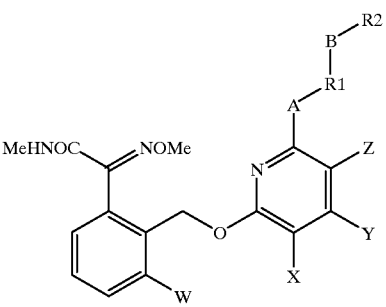

| Compound Number | W | X | Y | Z | A | $R^1$ | B | $R^2$ |
|---|---|---|---|---|---|---|---|---|
| 16 | —H | —Cl | —H | —Cl | O | —$CH_2CH_2$— | O | $C_2H_5OC_2H_4$— |
| 17 | —H | —H | —H | —H | O | —$CH_2CH_2$— | O | $C_2H_5$— |
| 18 | —H | —Cl | —H | —Cl | O | —$CH_2CH_2$— | O | $C_2H_5$— |
| 19 | —H | —Cl | —H | —Cl | O | —$CH_2CH_2$— | O | $C_3H_7OCH_2CH_2$— |
| 20 | —H | —Cl | —H | —Cl | C | —CH(OME)$CH_2$— | O | $CH_3$— |
| 21 | —H | —H | —H | —H | O | —$CH_2CH_2$— | O | $C_2H_5OC_2H_4$— |
| 22 | —H | —H | —H | —H | O | —CH(OME)$CH_2$— | O | $CH_3$— |

-continued

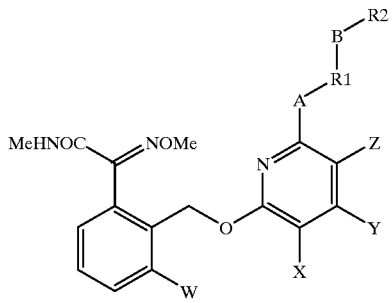

| Compound Number | W | X | Y | Z | A | R¹ | B | R² |
|---|---|---|---|---|---|---|---|---|
| 23 | —H | —Cl | —H | —Cl | NH | —CH$_2$CH$_2$— | O | C$_2$H$_5$— |
| 24 | —H | —H | —H | —Cl | O | —CH$_2$CH$_2$— | O | C$_2$H$_5$— |
| 25 | —H | —H | —H | —H | O | —CH$_2$CH$_2$— | O | CH$_3$— |
| 26 | —H | —Cl | —H | —Cl | O | —CH$_2$CH(CH$_3$)— | O | nC$_3$H$_7$— |
| 28 | —H | —Cl | —H | —Cl | O | —CH$_2$CH(CH$_3$)— | O | CH$_3$— |
| 29 | —H | —Cl | —H | —Cl | O | —CH$_2$CH$_2$— | O | nC$_3$H$_7$— |
| 30 | —H | —H | —H | —H | O | —CH$_2$CH(CH$_3$)— | O | CH$_3$— |
| 31 | —H | —H | —H | —H | O | —CH$_2$CH$_2$— | O | nC$_3$H$_7$— |
| 32 | —H | —H | —H | —H | O | —CH$_2$CH(CH$_3$)— | O | nC$_3$H$_7$— |
| 33 | —H | —Cl | —H | —Cl | O | —CH$_2$CH$_2$— | O | CH$_3$— |
| 34 | —H | —H | —H | —H | S | 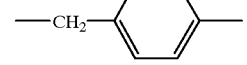 | O | CH$_3$— |
| 35 | —H | —H | —H | —H | S | 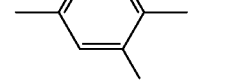 | O | CH$_3$— |
| 36 | —H | —H | —H | —H | O | —CH$_2$CH$_2$— | O | nC$_3$H$_7$— |
| 38 | —H | —H | —H | —H | O | 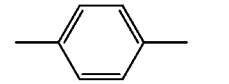 | O | CH$_3$— |
| 39 | —H | —H | —H | —H | S | 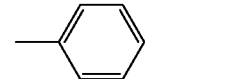 | O | CH$_3$— |
| 40 | —H | —H | —H | —H | S | 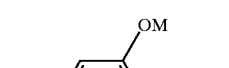 | O | CH$_3$— |
| 41 | —H | —H | —H | —H | S |  | O | CF$_3$— |

-continued

| Compound Number | W | X | Y | Z | A | R¹ | B | R² |
|---|---|---|---|---|---|---|---|---|
| 42 | —H | —H | —H | —H | S | 2,3-dimethylphenyl | O | $CH_3$— |
| 43 | —H | —H | —H | —H | S | 2,5-dimethylphenyl | S | $CH_3$— |
| 44 | —H | —H | —H | —H | S | 2,3-dimethyl-5-bromophenyl | O | $CF_3$— |
| 45 | —H | —H | —H | —H | O | —$CH_2CH_2$— | S | $C_2H_5$— |
| 46 | —H | —H | —H | —H | O | —$CH_2CH_2$— | O | $nC_4H_9$— |
| 47 | —H | —H | —H | —H | O | —$CH_2CH_2$— | S | $nC_4H_9$— |
| 48 | —H | —H | —H | —H | O | —$CH_2CH_2$— | S | $nC_4H_9$— |
| 49 | —H | —H | —H | —H | O | —$CH_2CH_2$— | O | Ph— |
| 50 | —H | —H | —H | —H | S | —$CH_2CH_2$— | S | $C_2H_5$— |
| 51 | —H | —H | —H | —H | O | —$CH_2CH_2$— | O | $PhCH_2$— |
| 52 | —H | —H | —H | —H | S | —$CH_2CH_2$— | S | $tC_4H_9$— |
| 53 | —H | —H | —H | —H | O | —$CH_2CH_2$— | O | $iC_3H_7$— |
| 54 | —H | —H | —H | —H | O | —$CH_2CH2CH_2$— | O | $iC_3H_7$— |
| 55 | —H | —H | —H | —H | O | —$CH_2CH2CH_2$— | O | $C_2H_5$— |
| 56 | —H | —H | —H | —H | O | —$CH_2CH_2$— | O | 2-Ethylhexyl- |
| 57 | —H | —H | —H | —H | S | —$CH_2$-(4-methylphenyl)- | O | $CH_3$— |
| 58 | —H | —H | —H | —H | O | —$CH_2CH_2$— | O | Cyclobutyl- |
| 59 | —F | —H | —H | —H | O | —$CH_2CH_2$— | O | $nC_3H_7$— |
| 60 | —Cl | —H | —H | —H | O | —$CH_2CH_2$— | O | $nC_3H_7$— |
| 61 | —H | —H | —H | —H | O | —$CH_2CH_2$— | O | $nC_5H_{11}$— |
| 62 | —H | —H | —H | —H | O | —$CH_2CH_2$— | O | Cyclohexyl- |
| 63 | —Cl | —H | —H | —H | O | —$CH_2CH_2$— | O | $C_2H_5$— |
| 64 | —H | —H | —H | —H | O | 2,3-dimethylphenyl | O | $C_2H_5$— |
| 65 | —H | —H | —H | —H | O | —$(CH_2)_4$— | O | $C_2H_5$— |
| 66 | —H | —H | —H | —H | O | —$(CH_2)_5$— | O | $PhCH_2$— |

-continued

[Structure: MeHNOC-C(=NOMe)-phenyl(W)-CH2-O-pyridine(N, X, Y, Z)-A-R1, with B-R2 branch]

| Compound Number | W | X | Y | Z | A | R¹ | B | R² |
|---|---|---|---|---|---|---|---|---|
| 67 | —H | —H | —H | —H | O | (m-phenylene) | O | C₂H₅— |
| 68 | —H | —H | —H | —H | O | (p-phenylene) | O | C₂H₅— |
| 70 | —H | —H | —H | —H | O | —CH₂CH₂— | O | nC₆H₁₃— |
| 71 | —H | —H | —H | —H | O | —CH₂CH2CH₂— | O | CH₃O(CH₂)₃— |
| 72 | —H | —H | —H | —H | O | —CH(CH=CH₂)CH₂— | O | CH₃— |
| 73 | —H | —H | —H | —H | O | —CH₂CH₂— | O | NCCH₂CH₂CH(OMe)— |
| 74 | —H | —H | —H | —H | O | —CH₂CH₂— | O | (glycidyl: oxiranyl-CH₂—) |
| 75 | —F | —H | —H | —H | O | —CH₂CH₂— | O | nC₅H₁₁— |
| 76 | —Cl | —H | —H | —H | O | —CH₂CH₂— | O | nC₅H₁₁— |
| 77 | —F | —H | —H | —H | O | —CH₂CH2CH₂— | O | C₂H₅— |
| 78 | —Cl | —H | —H | —H | O | —CH₂CH2CH₂— | O | C₂H₅— |
| 79 | —F | —H | —H | —H | O | —CH₂CH2CH₂— | O | iC₃H₇— |
| 80 | —Cl | —H | —H | —H | O | —CH₂CH2CH₂— | O | iC₃H₇— |
| 81 | —H | —H | —H | —H | O | (o-phenylene) | O | CH₃— |
| 82 | —H | —H | —H | —H | O | —CH₂-(o-phenylene)- | O | CH₃— |
| 83 | —H | —H | —H | —H | O | —CH₂-(p-phenylene)- | O | CH₃— |
| 84 | —H | —H | —H | —H | O | —CH₂-(phenylene with OMe)- | O | CH₃— |
| 85 | —H | —H | —H | —H | S | (p-phenylene) | O | C₂H₅— |

-continued

| Compound Number | W | X | Y | Z | A | R¹ | B | R² |
|---|---|---|---|---|---|---|---|---|
| 87 | —H | —H | —H | —H | S | *p-phenylene* | O | nC₃H₇— |
| 88 | —H | —H | —H | —H | O | —CH₂—(3-methyl-4-methoxyphenyl)— | O | CH₃— |
| 89 | —H | —H | —H | —H | O | —CH₂CH2CH₂— | O | nC₃H₇— |

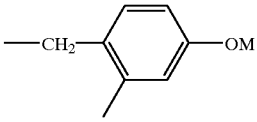

| Compound Number | W | X | Y | Z | —A—R¹—B—R² |
|---|---|---|---|---|---|
| 90 | —H | —H | —H | —H | 2,6-dimethylmorpholinyl |
| 91 | —H | —Cl | —H | —Cl | morpholinyl |
| 92 | —H | —Cl | —H | —Cl | 2,6-dimethylmorpholinyl |
| 93 | —H | —H | —H | —H | morpholinyl |

The compounds of formula (1) thus produced are usually obtained as a mixture of the E and Z forms, which can then be separated, via standard means known in the art, into each of those forms, if desired.

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion.

As used herein, the term "disease inhibiting and phytologically acceptable amount", refers to an amount of a compound of the present invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/Acre.

While the compounds of the present invention have significant activity for agricultural use, such as, for example, for use with agricultural crops, many of the compounds are effective for use with horticultural plants, stored grain and other non-plant loci, such as, for example, wood, paint, leather or carpet, to protect such materials from fungal infestation.

The following experiments were performed in the laboratory to determine the fungicidal efficacy of the compounds of the invention.

Compound Formulation: Compound formulation was accomplished by dissolving technical materials in acetone, with serial dilutions then made in acetone to obtain desired rates. Final treatment volumes were obtained by adding nine volumes 0.05kOO aqueous Tween-20 or Triton X-100, depending upon the pathogen.

Downy Mildew of Grape (*Plasmogara viticola*-PLASVI) (96 Hour Protectant): Vines (cultivar Carignane) were grown from seed in a soilless peat-based potting mixture (Metromix) until the seedlings were 10–20 cm tall. These plants were then sprayed to run off with the test compound at a rate of 100 ppm. After 96 hours the test plants were inoculated by spraying with an aqueous sporangia suspension of Plasmopara viticola. The plants were then transferred to the greenhouse until disease developed on the untreated control plants.

Powdery Mildew of Wheat (*Erysiphe graminis*-ERYSGT): Wheat (cultivar Monon) was grown in a soilless peat-based potting mixture (Metromix) until the seedlings were 1–2 leaf (BBCH 12). These plants were then inoculated with *Erysiphe graminis* by dusting spores from stock plants onto the test plants. After 48 hours the plants were sprayed to run off with the test compound at a rate of 25 ppm and then kept in the greenhouse until disease developed on the untreated control plants.

Glume blotch of wheat (*Leptosphaeria nodorum*-LEPTNO): Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Leptosphaeria nodorum*. The plants were then transferred to the greenhouse until disease developed on the untreated control plants. Brown rust (*Puccinia recondita*-PUCCRT): Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Puccinia recondita*. The plants were then transferred to the greenhouse until disease developed on the untreated control plants.

Septoria leaf spot (*Septoria tritici*-SEPTTR): Wheat (cultivar Monon) was grown from seed in a soilless peat-based potting mixture (Metromix) until the seedlings were 1–2 leaf (BECH 12). These plants were then sprayed to run off with the test compound at a rate of 100 ppm. After 24 hours the test plants were inoculated with an aqueous spore suspension of *Septoria tritici*. The plants were then transferred to the greenhouse until disease developed on the untreated control plants.

The following table presents the activity of typical compounds of the present invention when evaluated in these experiments. The effectiveness of the test compounds in controlling disease was rated using the following scale:

| Compound Number | PLASVI | ERYSGT | LEPTNO | PUCCRT | SEPTTR |
|---|---|---|---|---|---|
| 1 | ++ | + | ++ | ++ | |
| 2 | ++ | + | ++ | ++ | |
| 3 | ++ | + | | | |
| 4 | − | − | | | |
| 5 | ++ | − | | | |
| 6 | | ++ | | | |
| 7 | + | ++ | | | |
| 8 | ++ | − | | | |
| 9 | ++ | + | | | |
| 10 | + | ++ | | | |
| 11 | ++ | | | | |
| 12 | − | − | | | |
| 13 | + | − | + | | |
| 14 | | | | | |
| 15 | ++ | ++ | | | |
| 16 | ++ | ++ | + | | |
| 17 | ++ | + | ++ | | |
| 18 | ++ | + | ++ | | |
| 19 | + | + | ++ | | |
| 20 | + | + | + | | |
| 21 | ++ | | + | | |
| 22 | + | ++ | + | | |
| 23 | ++ | ++ | | | |
| 24 | ++ | ++ | + | | |
| 25 | ++ | ++ | | | |
| 26 | + | ++ | | | |
| 27 | + | + | | | |
| 28 | ++ | ++ | | | |
| 29 | ++ | + | | | |
| 30 | ++ | ++ | | | |
| 31 | ++ | ++ | | | |
| 32 | | ++ | | | |
| 33 | ++ | + | | | |
| 34 | ++ | ++ | | | |
| 35 | ++ | | | | |
| 36 | ++ | + | | | |
| 37 | | ++ | ++ | | |
| 38 | | ++ | | | |
| 39 | | ++ | | | |
| 40 | ++ | + | | | |
| 41 | ++ | + | | | |
| 42 | ++ | ++ | | | |
| 43 | ++ | − | | | |
| 44 | ++ | ++ | | | |
| 45 | ++ | + | | | |
| 46 | ++ | + | | | |
| 47 | ++ | ++ | | | |
| 48 | + | − | | | |
| 49 | ++ | ++ | | | |
| 50 | ++ | − | | | |
| 51 | ++ | ++ | | | |
| 52 | ++ | ++ | + | | |
| 53 | ++ | ++ | − | | |
| 54 | ++ | ++ | ++ | | |
| 55 | + | + | | | |
| 56 | ++ | | | | ++ |
| 57 | ++ | | | | ++ |
| 58 | ++ | | | | ++ |
| 59 | ++ | | | | |
| 60 | ++ | | | | ++ |
| 61 | ++ | | | | ++ |
| 62 | ++ | | | | + |
| 63 | ++ | | | | |
| 64 | ++ | | | | ++ |
| 65 | ++ | | | | ++ |
| 66 | ++ | | | | ++ |
| 67 | ++ | | | | |
| 68 | ++ | | | | + |
| 69 | ++ | | | | |
| 70 | + | | | | + |
| 71 | | | | | − |
| 72 | | | | | − |
| 73 | | | | | − |
| 74 | | | | | ++ |
| 75 | | | | | ++ |
| 76 | | | | | ++ |
| 77 | | | | | ++ |
| 78 | | | | | ++ |
| 79 | | | | | ++ |
| 80 | | | | | ++ |
| 81 | | | | | + |
| 82 | | | | | ++ |
| 83 | | | | | ++ |
| 84 | | | | | ++ |
| 85 | | | | | − |
| 86 | ++ | | | | + |
| 87 | | ++ | | | |
| 88 | ++ | + | ++ | | + |
| 89 | − | + | − | | | blank space = not tested
− = 0–24% control of plant disease
+ = 25–74% control of plant disease
++ = 75–100 % control of plant disease The compounds of this invention are preferably applied in the form of a composition comprising one or more of the compounds of formula (1) with a phytologically-acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the compounds of this invention can be formulated for delivery for use as a fungicide. As will be readily appreciated, any material to which these compounds can be added may be used, provided they yield the desired utility without significant interference with activity of the compounds of this invention as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds of this invention comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of this invention, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been preformed to the appropriate particle size, in the range of from about 0.5 to about 3 mm. Such compositions may also be formulated by making a dough or paste of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5%.

Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The composition may optionally include fungicidal combinations which comprise at least li of one or more of the compounds of this invention with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1.

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds of this invention or compositions. The compounds are suitable for treatment of various plants at fungicidal levels, while exhibiting low phytotoxicity. The compounds are useful in a protectant or eradicant fashion. The compounds of this invention are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds of this invention have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungi species: Downy Mildew of Grape (*Plasmopara viticola*-PLASVI), Late Blight of Tomato (Phytophthora infestans - PHYTIN), Apple Scab (*Venturia inaequalis*-VENTIN), Brown Rust of Wheat (*Puccinia recondita*-PUCCRT), Stripe Rust of Wheat (*Puccinia striiformis*-PUCCST), Rice Blast (*Pyricularia oryzae*-PYRIOR), Cercospora Leaf Spot of Beet (*Cercospora beticola*-CERCBE), Powdery Mildew of Wheat (*Erysiphe graminis*-ERYSGT), Leaf Blotch of Wheat (*Septoria tritici*-SEPTTR), Sheath Blight of Rice (*Rhizoctonia solani*-RHIZSO), Eyespot of Wheat (*Pseudocercosporella herpotrichoides*-PSDCHE), Brown Rot of Peach (*Monilinia fructicola*-MONIFC), Glume Blotch of Wheat (*Septoria nodorum*-LEPTNO). It will be understood by those in the art that the efficacy of the compounds of this invention for the foregoing fungi establishes the general utility of the compounds as fungicides.

The compounds of this invention have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the compounds of this invention, and compositions containing the same, may not be equally effective at similar concentrations or against the same fungal species. The compounds of this invention and compositions are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

What is claimed is:

1. A compound of Formula (1)

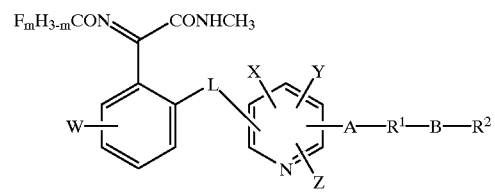

Formula (1)

wherein m is an integer 0–3;

L is —CH$_2$O— or —CH$_2$—S—;

X, Y, and Z are each independently H, C$_{1-6}$ alkyl, C$_{1-6}$ alkoxy, halo-C$_{1-6}$ alkyl, halo-C$_{1-6}$ alkoxy, halo, nitro, carbo-C$_{1-6}$ alkoxy, cyano, C$_{1-6}$ alkylthio, or halo-C$_{1-6}$ alkylthio;

W is H, halogen, C$_{1-4}$ alkyl, C$_{1-4}$ alkoxy, halo-C$_{1-4}$ alkyl, or C$_{1-4}$ alkylthio;

A is O, S, NR$^3$, OCH$_2$, SCH$_2$;

B is O or S;

R$^1$ is a C$_1$–C$_4$ alkyl group (optionally substituted by alkenyl, cycloalkyl, alkoxy, alkoxycarbonyl, aralkyl, cyano, cyanoalkyl, halo, or haloalkyl), optionally substituted aryl or heteroaryl ring;

R$^2$ is a C$_1$–C$_8$ alkyl (optionally substituted by alkenyl, cycloalkyl, alkoxy, alkoxycarbonyl, aralkyl, cyano, cyanoalkyl, halo, or haloalkyl), an optionally substituted aryl or heteroaryl ring; and R$^3$ is H or C$_{1-6}$ alkyl.

2. A compound of claim 1 of the formula

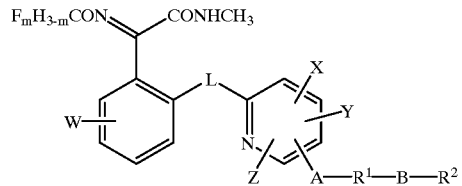

wherein the substituents are as defined in claim 1.

3. A compound of claim 2 of the formula

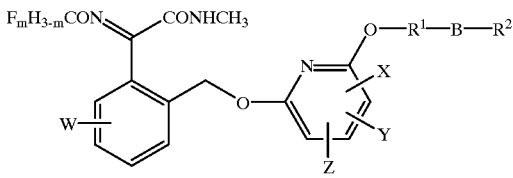

wherein the substituents are as defined in claim 1.

4. A compound of claim 3 of the formula

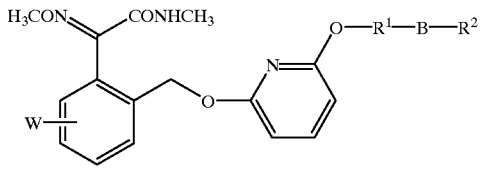

wherein the substituents are as defined claim in 1.

5. A compound of claim 4 of the formula

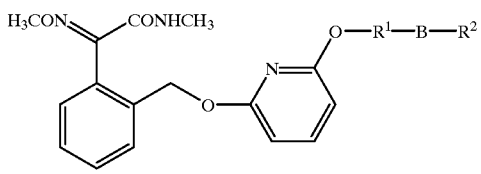

wherein the substituents are as defined in claim 1.

6. A compound of claim 5 wherein $R^1$—B—$R^2$ is —$CH_2CH_2$—O—$nC_3H_7$.

7. A compound of claim 5 wherein $R^1$—B—$R^2$ is

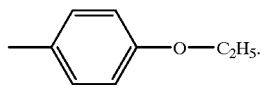

8. A fungicidal composition comprising the compound of claim 1 and a phytologically acceptable carrier.

9. A fungicidal method which comprises applying to the locus to be treated a fungicidally-effective amount of a compound of formula (1)

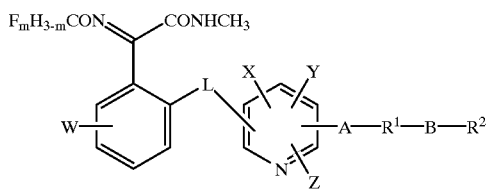

Formula (1)

wherein
m is an integer 0–3;
L is —$CH_2O$— or —$CH_2S$—;
X, Y, and Z are each independently H, $C_{1-6}$ alkyl, $C_{1-6}$ alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-6}$ alkylthio;
W is H, halogen, $C_{1-4}$ alkyl, $C_{1-4}$ alkoxy, halo-$C_{1-4}$ alkyl, or $C_{1-4}$ alkylthio;
A is O, S, $NR^3$, $OCH_2$, $SCH_2$;
B is O or S;
$R^1$ is a $C_1$–$C_4$ alkyl group (optionally substituted by alkenyl, cycloalkyl, alkoxy, alkoxycarbonyl, aralkyl, cyano, cyanoalkyl, halo, or haloalkyl), optionally substituted aryl or heteroaryl ring;
$R^2$ is a $C_1$–$C_8$ alkyl (optionally substituted by alkenyl, cycloalkyl, alkoxy, alkoxycarbonyl, aralkyl, cyano, cyanoalkyl, halo, or haloalkyl), an optionally substituted aryl or heteroaryl ring; and
$R^3$ is H or $C_{1-6}$ alkyl.

10. A compound of Formula (1)

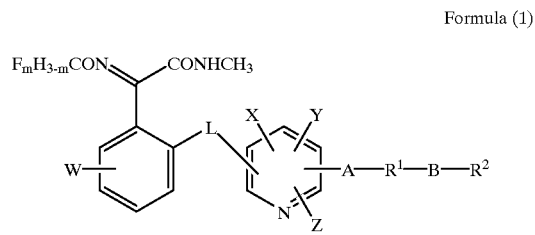

Formula (1)

wherein
m is an integer 0–3;
L is —$CH_2O$— or —$CH_2S$—;
X, Y, and Z are each independently H, $C_{1-6}$ alkyl, $C_{1-6}$ alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-6}$ alkylthio;
W is H, halogen, $C_{1-4}$ alkyl, $C_{1-4}$ alkoxy, halo-$C_{1-4}$ alkyl, or $C_{1-4}$ alkylthio;
A is O, S, $NR^3$, $OCH_2$, $SCH_2$;
—$R^1$—B—$R^2$ is 2,2-dimethyl-1,3-dioxolan-4-yl; and
$R^3$ is H or $C_{1-6}$ alkyl.

11. A fungicidal composition comprising the compound of claim 10 and a phytologically acceptable carrier.

12. A fungicidal method which comprises applying to the locus to be treated a fungicidally-effective amount of a compound of formula (1)

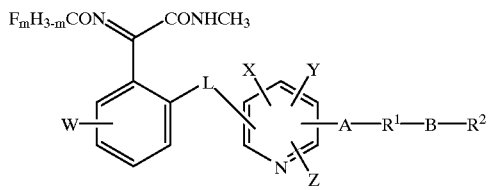

Formula (1)

wherein
m is an integer 0–3;
L is —$CH_2O$— or —$CH_2S$—;
X, Y, and Z are each independently H, $C_{1-6}$ alkyl, $C_{1-6}$ alkoxy, halo-$C_{1-6}$
alkyl, halo-$C_{1-6}$ alkoxy, halo, nitro, carbo-$C_{1-6}$ alkoxy, cyano, $C_{1-6}$ alkylthio, or halo-$C_{1-4\ 6}$ alkylthio;
W is H, halogen, $C_{1-4}$ alkyl, $C_{1-4}$ alkoxy, halo-$C_{1-4}$ alkyl, or $Ch_{1-4}$ alkylthio;
A is O, S, $NR^3$, $OCH_2$, $SCH_2$;
—$R^3$—B—$R^2$ is 2,2-dimethyl-1,3-dioxolan-4-yl; and
$R^3$ is H or $C_{1-6}$ alkyl.

* * * * *

UNITED STATES PATENT AND TRADEMARK OFFICE
CERTIFICATE OF CORRECTION

PATENT NO. : 6,369,083 B1
DATED : April 9, 2002
INVENTOR(S) : Emily J. Canada et al.

It is certified that error appears in the above-identified patent and that said Letters Patent is hereby corrected as shown below:

Title page,
Title should read -- 2-METHOXYLIMINO-2-(PYRIDINYLOXYMETHYL) PHENYL ACETAMIDES WITH POLYETHER DERIVATIVES ON THE PYRIDINE RING -- rather than "2-METHOXYLIMINO-2-(PYRINYLOXYMETHYL) PHENYL ACETAMIDES WITH POLYETHER DERIVATIVES ON THE PYRIDINE RING"

Column 30,
Lines 58-60, should read -- alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-6}$ alkylthio -- rather than "alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-4\,6}$ alkylthio"
Line 62, should read -- or $C_{1-4}$ alkylthio -- rather than "or $Ch_{1-4}$ alkylthio"

Signed and Sealed this

Third Day of September, 2002

Attest:

JAMES E. ROGAN
Attesting Officer   Director of the United States Patent and Trademark Office

UNITED STATES PATENT AND TRADEMARK OFFICE
CERTIFICATE OF CORRECTION

PATENT NO. : 6,369,083 B1
DATED : April 9, 2002
INVENTOR(S) : Emily J. Canada et al.

It is certified that error appears in the above-identified patent and that said Letters Patent is hereby corrected as shown below:

<u>Title page,</u>
Title should read -- 2-METHOXYLIMINO-2-(PYRIDINYLOXYMETHYL) PHENYL ACETAMIDES WITH POLYETHER DERIVATIVES ON THE PYRIDINE RING -- rather than "2-METHOXYLIMINO-2-(PYRINYLOXYMETHYL) PHENYL ACETAMIDES WITH POLYETHER DERIVATIVES ON THE PYRIDINE RING"

<u>Column 30,</u>
Lines 58-60, should read -- alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-6}$ alkylthio -- rather than "alkoxy, halo-$C_{1-6}$ alkyl, halo-$C_{1-6}$ alkoxy, halo, nitro, carbo-$C_{1-6}$ alkoxy, cyano, $C_{1-6}$ alkylthio, or halo-$C_{1-4,6}$ alkylthio"
Line 62, should read -- or $C_{1-4}$ alkylthio -- rather than "or $Ch_{1-4}$ alkylthio"
Line 64, should read -- -$R^1$-B-$R^2$ is 2,2-dimethyl-1,3-dioxolan-4-yl; and -- rather than "$R^3$-B-$R^2$ is 2,2-dimethyl-1,3-dioxolan-4-yl; and"

This certificate supersedes Certificate of Correction issued September 3, 2002.

Signed and Sealed this

Twelfth Day of November, 2002

*Attest:*

*Attesting Officer*

JAMES E. ROGAN
*Director of the United States Patent and Trademark Office*